(12) United States Patent
Vargas Fonseca

(10) Patent No.: US 11,052,179 B2
(45) Date of Patent: Jul. 6, 2021

(54) CHAMBER FOR ARTIFICIAL CIRCULATORY ASSISTANCE AND MEMBRANE

(71) Applicant: ZAMMI INSTRUMENTAL LTDA, Duque de Caxias (BR)

(72) Inventor: Luiz Henrique Vargas Fonseca, Duque de Caxias (BR)

(73) Assignee: ZAMMI INSTRUMENTAL LTDA, Rio de Janeiro (BR)

( * ) Notice: Subject to any disclaimer, the term of this patent is extended or adjusted under 35 U.S.C. 154(b) by 109 days.

(21) Appl. No.: 15/314,036

(22) PCT Filed: May 26, 2014

(86) PCT No.: PCT/BR2014/000166
§ 371 (c)(1),
(2) Date: Nov. 25, 2016

(87) PCT Pub. No.: WO2015/179929
PCT Pub. Date: Dec. 3, 2015

(65) Prior Publication Data
US 2017/0112984 A1    Apr. 27, 2017

(51) Int. Cl.
*A61M 1/10* (2006.01)
*A61M 1/12* (2006.01)

(52) U.S. Cl.
CPC ........ *A61M 1/1005* (2014.02); *A61M 1/1006* (2014.02); *A61M 1/1037* (2013.01); *A61M 1/1096* (2014.02); *A61M 1/12* (2013.01); *A61M 1/122* (2014.02); *A61M 1/106* (2013.01); *A61M 1/1098* (2014.02)

(58) Field of Classification Search
CPC ...... A61M 1/12; A61M 1/122; A61M 1/1008; A61M 1/1037; A61M 1/1086; A61M 1/1098; A61M 1/1005; A61M 1/1006; A61M 1/1096
USPC .................................................. 600/116, 16
See application file for complete search history.

(56) References Cited

U.S. PATENT DOCUMENTS

| | | | | |
|---|---|---|---|---|
| 3,883,272 A | * | 5/1975 | Puckett | F04B 9/02 417/383 |
| 4,077,882 A | * | 3/1978 | Gangemi | A61M 1/3639 210/137 |
| 4,104,005 A | * | 8/1978 | Poirier | F04B 43/10 285/281 |
| 6,497,675 B1 | * | 12/2002 | Davankov | A61M 1/3472 210/433.1 |
| 7,029,245 B2 | | 4/2006 | Maianti et al. | |
| 7,273,465 B2 | | 9/2007 | Ash | |

(Continued)

FOREIGN PATENT DOCUMENTS

EP        1099455 A3 *  5/2001  ............ A61M 39/24

*Primary Examiner* — Mallika D Fairchild
*Assistant Examiner* — Minh Duc G Pham
(74) *Attorney, Agent, or Firm* — Muncy, Geissler, Olds and Lowe, P.C.

(57) ABSTRACT

A novel artificial circulatory assistance chamber for various uses associated with cardiovascular procedures, having a rigid capsule with a base and a dome, with blood inlet connectors and blood outlet connectors, and respective one-way valves. The rigid capsule contains an impermeable membrane that divides the capsule into a blood compartment and an outer compressible compartment that is filled with a volume of gas/liquid.

18 Claims, 6 Drawing Sheets

(56) References Cited

U.S. PATENT DOCUMENTS

2013/0053625 A1* 2/2013 Merce Vives .......... A61M 1/10
 600/16
2013/0343936 A1* 12/2013 Gray ...................... F04B 53/16
 417/437

* cited by examiner

FIGURE 4 *(Prior art)*
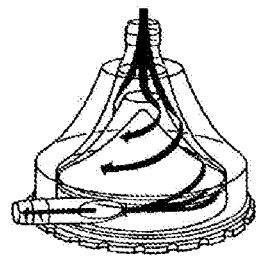
FIGURE 5 *(Prior art)*
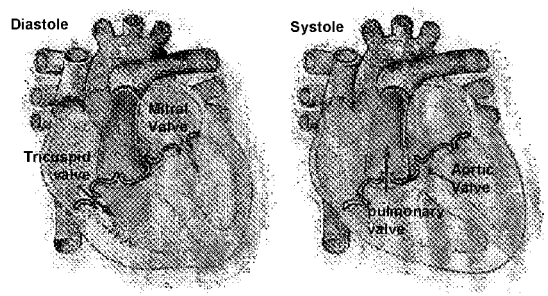
FIGURE 6a *(Prior art)*      FIGURE 6b *(Prior art)*
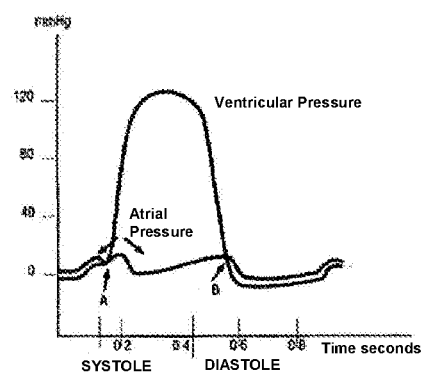 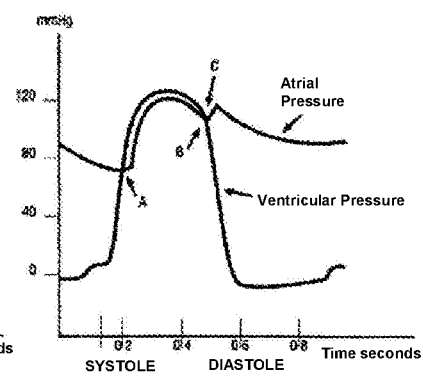

CHAMBER FOR ARTIFICIAL CIRCULATORY ASSISTANCE AND MEMBRANE

FIELD OF THE INVENTION

The present invention refers to a new chamber for artificial circulatory assistance that, within the several applications in which its importance and performance are emphasized, has the one related to cardiovascular procedures, notably for producing arterial capacitance, regulating blood pressure and producing aortic counterpulsation.

The chamber according the present invention can be applied in the most different situations, as a provisional or definitive implantable medical device for acting as a cardiovascular orthosis or prosthesis with functions of, among others, dampening the blood pressure peak and blood pumping, generating compliance in the arterial line of the extracorporeal circulation circuit during cardiovascular surgical procedures that require the use of this technique, ventricular assistance device (VAD), aortic counterpulsation, optimization of aortic compliance on patients suffering from resistant hypertension and reduced arterial distensibility, pumping device for draining the cavity and pumping device for aspiration of the cavity.

The present invention also refers to a membrane particularly developed to be used in fluid circulation chambers, such as the one mentioned above.

BACKGROUND

The extracorporeal circulation (ECC) is a technique used in cardiovascular procedures that allows to temporarily replacing the cardiopulmonary functions. The heart pumping functions are performed by a mechanical pump and the lung functions are replaced by an apparatus capable of performing gas exchanges with blood interconnected in series by a plastic manifold circuit. FIG. 1 illustrates an extracorporeal circulation basic circuit with membranes oxygenator which comprises a cardiotomy reservoir (1), oxygen chamber (3), venous line (3), arterial line (4), arterial return line filter (5), arterial filter (6), arterial pump (7), suction pumps (8), ventricular decompression pump (9), cardioplegia delivery system (10), crystalloid cardioplegia (11), water inlet line (12), water outlet line (13) and gas line (14). This is an extracorporeal circulation circuit, wherein the structure and functioning are well known by the person skilled in the art.

It is further known that the extracorporeal circulation is a procedure ruled by physiological principles, which under some circumstances could be required over periods of 1 hour, 2 hours and even weeks. In these cases, the physiological deviations are more marked and, consequently, result in more complications to the organism. The great functional differences between the human organism and the artificial organs reflect on the human body reaction during and right after the ECC. Hundreds surgeries are performed worldwide every day. The recovery with no consequences is the most common result. However, some patients could present important complications produced by hypoxia, embolism, coagulopathy and blood dyscrasia, cerebral edema or edema of other organs, as well as alterations related to the exacerbated response of the organism protection and defense systems which could produce complications in different levels of implications, which could act on preexisting morbidities and cause death. The high resistance of the flow generated by the membrane in the oxygenation chamber traumatizes the blood and activates the platelets. The ECC long circuits require high filling volumes (prime), which leads to the blood hemodilution that, when wrongly dimensioned, affects the oxygen transportation, excessively reduces blood viscosity and oncotic pressure that associated to the continuous flow produced by the non pulsatile flow pump leads to the altering of the capillary permeability and consequential formation of interstitial edema.

FIG. 2 illustrates a diagram of blood pressure behavior to show that the mechanical pumping produces a linear flow, i.e., without the occurrence of pulsation. In this Figure, it is verified the pre-bypass phase (A), the period of partial bypass (B), total bypass (C), the period between (C) and (D), corresponding to the hypertension of the perfusion outset. It is also observed that the blood pressure stabilizes up to the beginning of the elevation by the action of the catecolamines and other natural vasopressors and indicates the greater elevation of the blood pressure, after 30 or 40 minutes from the perfusion, being observed, afterwards, the perfusion output (F).

The control mechanisms of the receptor sensitive to the pulse are absent on ECC with linear flow. The absence of arterial pulse triggers a series of events that results on the release of vasoactive substances in the blood flow, determining the closure of the arterioles and reduction of the perfusion in capillary periphery that results on the induction of a syndrome identified as Systemic Inflammatory Response Syndrome and poor perfusion of the tissues.

The ECC traditional technique consists basically in simulating the circulatory system connected to an oxygenator device capable of promoting gas exchanges in the blood, extracting carbon dioxide and providing oxygen, a thermal exchanger coupled to the oxygenator device. This circuit is assembled in a heart-lung machine. The system is prepared and connected to a patient parallel to the normal circulatory system, by venoarterial access. The circuit is connected to the venous access by a cannula inserted in the right atrium or by two cannulas in the superior and inferior vena cava. Blood is drained through the venous line aperture to the venous reservoir, blood collecting device and, afterwards, reaches the blood pumping device which produces the blood flow according to the patients needs. Then, the blood reaches the oxygenator coupled to a heat exchanger system that enables controlling of the flow temperature when it passes through it. The temperature exchange occurs after blood has reached the oxygenation chamber where it suffers the gas exchanges. The oxygenation chamber contains an amount of hollow and microporous microfibers that are internally traveled by the air mixture flow enriched with oxygen and externally traveled by the blood flow. A continuous supply of air mixture enriched with oxygen is connected to the oxygenation chamber, providing oxygen to the blood while removes the excess of carbon dioxide. After the oxygenation, blood returns to the normal arterial circulation through an arterial access cannula.

Specifically, the blood pumping is executed by a peristaltic pump, a compressing pump segment is assembled on the roller pump pocket. The rollers are placed in a 180° angle related to the each other in a semi circular pocket with 210° angle and they are adjusted to compress the tube segment in its path over it, thus when it is compressed, the piping pushes its content from point A to point B.

FIG. 3 illustrates this two-roller-pump that was adopted due to its mechanical simplicity, easy of assembly and the usage and safety provided. The flow generated by such is linear, not pulsatile. The pump is electrically operated, but can also be triggered manually, by means of cranks coupled to the roller axes in case an electrical or mechanical failure of the equipment occurs. If it is not used properly, the roller pump could suck and pump air, which generates extremely severe complications. The adjustment of the distance between the roller and the rigid bed wherein it passes is critical to the correct functioning of the pump and it is called roller calibration. The calibration point is the occlusive point of the tube segment. Another disadvantage of using this type of pump is the increased negative pressure that it applies to the inlet hole for sucking the fluid to be propelled. A roller excessively tight, beyond the occlusive point, increases blood trauma, which could produce pronounced hemolysis. A roller excessively lose allows reflux, causes swirling and hemolysis, besides stimulating variable blood volumes according to the resistance status of the perfused arteriolar system.

An alternative to the roller pump provided by the state of the art is the centrifugal pump illustrated in FIG. 4. The centrifugal pump is known as kinetic pump, i.e., a pump wherein blood propulsion action is performed by adding kinetic energy generated by the rotation of a rotor element. In the most common type of centrifugal pump, there is a set of concentric cones, in which the outer polycarbonate cone contains a central inlet hole and a lateral outlet hole wherein correspondent lines are adapted. The inner cone has a magnetic coupling with an external rotor that makes it spin in a high rotation per minute. The rotation of the inner cone makes the other cones to rotate. This produces a vortex effect and its transmission produces a blood flow. In this type of pump, it is observed that the inconvenience of hemolysis production still remains, and as well as in modern roller pumps and under some conditions, it could also push the air. Another aspect to be considered is that in this pump there is no previous charge and the flow depends directly on the number of rotations per minute of the inner cone. The flow varies according to the peripheral vascular resistance against which the pump pushes blood. When the rotation speed of the cone is decreased, the blood flow is reduced; when the patient's peripheral resistance increases, the pump flow reduces too. If the constant speed (rpm) is maintained and the patient's peripheral vascular resistance is reduced, the blood flow substantially increases. In order that this type of pump is properly working, it is essential having a flow meter coupled to it. The pump flow cannot be relieved otherwise.

As it is observed, both types of pumps described above are currently used in ECC as a blood pumping device, however, both are propellers generating linear and continuous blood flow.

Physiologically, the blood flow is pulsatile ad morphologically is the result of a cardiac cycle. Briefly, the cardiac cycle comprises a systole (contraction) and a diastole (relaxing). The contraction and relaxing of heart chambers result in pressure alterations within them, which produce blood movement through the cardiovascular system, according to the illustration in FIG. 4. Cyclically, blood comes into the vena cava to the heart, and it accumulates in the right atrium, after the opening of the tricuspid valve, it reaches the right ventricle in its relaxing phase, after filling, the ventricle contracts, the tricuspid valve closes and the pulmonary valve opens directing the blood flow to the pulmonary artery. Blood flows to the lungs and returns through pulmonary vessels which converge into the left atrium and reach the left ventricle through the opening of the mitral valve. The contraction of the left ventricle closes the mitral valve and opens the aortic valve, determining the blood flow for the systemic circulation, the myocardial contraction, the closure and opening of the valves, the blood volume ejected in the systemic circulation. This cycle produces a great variation in blood pressure, i.e., the pressure wave.

In each cardiac cycle, it is ejected an amount of blood into the arteries (systolic volume) and the frequency of the cycles produces the cardiac debt, whose intensity produces the blood flow in the arteries and, at the same time, determines the strength against the flow, this is called resistance. The relation between the flow and the resistance determines the blood pressure. The blood pressure presents morphology of a wave with pressure peaks (systolic pressure) and wave depression (diastolic pressure). The systolic and diastolic pressure difference is the arterial pulse.

In the attempt to make the flow more similar to the flow from the reciprocating cardiac pump, several researchers have proposed modifications in the conventional pumps in order to provide a pulsatile flow. In terms of hemodynamic and metabolic behavior, the undesirable effects of the linear flow are reduced or eliminated by the perfusion with pulsatile flow. There is a solid theoretical and experimental fundamentals showing the advantages of the pulsatile flow in extracorporeal circulation. The main reasons for a better tissue perfusion with pulsatile flow are the energy from the pulse wave, the pressure from the closure of the capillaries and the controlling mechanisms of the receptors sensitive to the pulse wave. The energy of the pulse wave is important in its transmission to the capillaries of the tissues, favoring the tissue perfusion, while the diastolic phase of pulse wave keeps the capillaries opened for a longer period, favoring fluid exchanges with interstitial fluid. Various receptors of the arterial system depend on the pressure variation and the pulse wave for issuing regulatory stimuli of the vascular tonus and hormone release. These factors are, in a certain extent, responsible for the elevation of the peripheral arterial resistance that occurs in the perfusion with linear flow. Several experimental and clinical studies have shown that cerebral, renal and other organs perfusion is superior with pulsatile flow, which also produces less metabolic acidosis and keeps normal vascular resistance.

FIG. 6a illustrates a diagram showing the intraventricular and atrial pressure behavior during the cardiac cycle. Point (A) indicates the closure of atrioventricular valves and point (B) indicates the opening moment of them. FIG. 6b illustrates a diagram showing the aortic and left ventricular pressures behavior during the cardiac cycle. Point (A) indicates the opening moment of the aortic valve and point (B) the moment of its closure, which determines an incision in aortic pressure curve.

Other studies and practical experiences show that the arterial cannula hole reduces the transmission of the pulse wave to the patient's circulatory system, besides increasing cellular trauma and hemolysis. Various mechanisms were developed in the attempt of producing viable pulsatile flow, however, most of them did not establish advantages effectively comparable to the linear pumping system, due mostly because they included a device that would produce pulse into the ECC circuit line, although the pumping being executed by a pump of linear flow. The patent application PI0803331-5A2 illustrates this attempt.

Thus considered, it is the object of the present invention to provide a chamber for artificial circulatory assistance that effectively solves the problems from the state of the art mentioned above, besides making possible, in an advantageous way, the provision of an ECC with linear pumping.

BRIEF DESCRIPTION OF THE DRAWINGS

The present invention will be described in reference to the attached drawings that are only for illustration purpose, not limitative of the scope of this invention, in which:

FIG. 4 illustrates a prior art centrifugal pump;

FIG. 5 illustrate a prior art physiological cardiac blood flow;

FIG. 6a illustrates a prior art diagram showing the intraventricular and atrial pressure behavior during the cardiac cycle;

FIG. 6b illustrates a prior art diagram showing the aortic and left ventricular pressures behavior during the cardiac cycle;

DETAILED DESCRIPTION OF THE INVENTION

Figure 1:
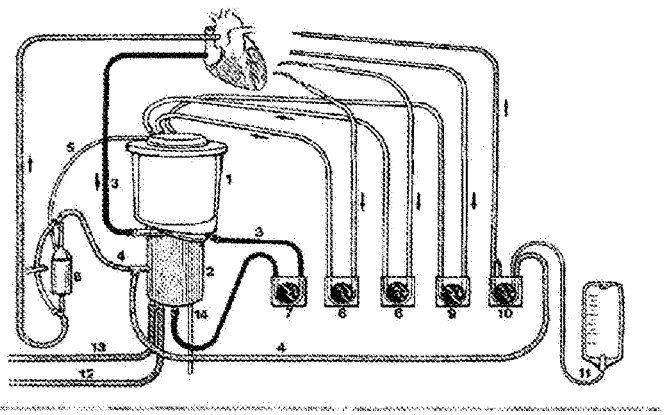
FIG. 1 illustrates a prior art extracorporeal circulation basic circuit with membranes oxygenator.
Figure 2:
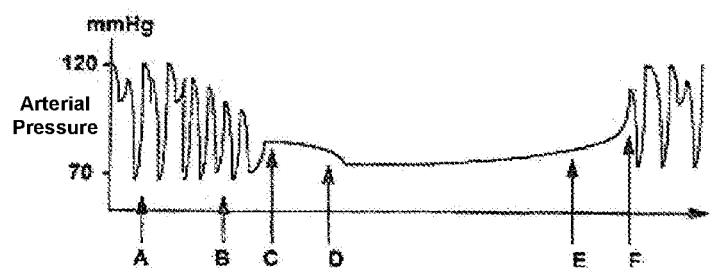
FIG. 2 illustrates a prior art diagram of blood pressure behavior.
Figure 3:
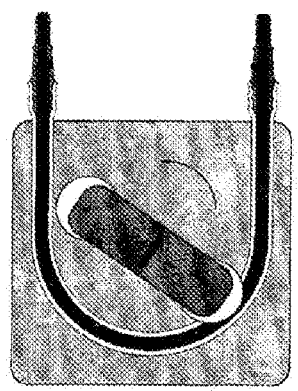
FIG. 3 illustrates a prior art two-roller-pump.
Figure 7:
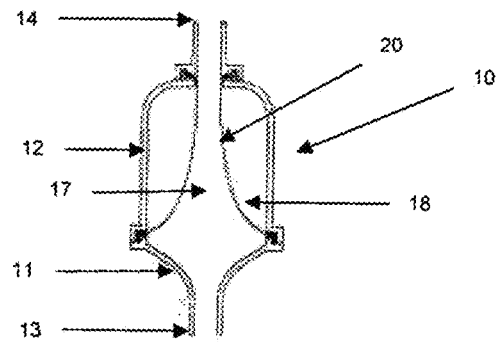
FIG. 7 illustrates a schematic sectional view from the chamber for circulatory assistance according to the present invention.

FIG. 7 illustrates the chamber for artificial circulatory assistance object of the present invention when applied as a damping device of the arterial pulse wave.

A pulsation dampener acts absorbing the pressure peaks generated by the pump and, thus, it allows smoothing the pressure curve, stabilizing flow oscillations, producing constant and linear hydraulic flow. Generally, it is formed by a volume chamber assembled adjoined to the hydraulic piping, it has an inner space to absorb volume and pressure. This inner space is filled with determined gas volume insulated by means of a resilient membrane. A pressure variation in the hydraulic circuit during the pumping acts on the chamber and generates compressing of its air volume during the pressure peak produced by the pump, this makes the chamber to retain part of the flow volume generated by the pumping in the pressure peak moment, the inner air of the chamber is compressed and, consequently, it builds up pressure. This pressure will be returned to the circuit in the suction phase of the pump, moment of the pumping cycle wherein the pressure of the circuit becomes lower than the pressure accumulated by the compressed air.

The gases thermodynamic establishes that "when the gas is compressed by an external pressure, the means loses energy and the system gains it, at the same time, when it expands against the external pressure of the means, it spends energy in the work form to achieve the expansion. In this case, the system loses energy and, according to the principle of energy conservation, the means gains the same amount". This concept is applied to devices commercially available for the application in various volumetric displacement driving pumping circuits. But there is no use in medical purposes, in the field of medical devices.

The vascular system is extensible, i.e., it has the ability to accommodate more blood volume in its compartment through the variation of muscular tonus, in the arteries it allows the accommodation of the pulsatile debt from the heart, making the pressure peak being relieved and the blood flow to the little vessels to be continuous and uniform with minimal pulses, this attribute is the Compliance. The arterial compliance reduces with the aging that enhances the effects of arterial hypertension.

As smaller is the compliance of the arterial system, bigger is going to be the elevation of the pressure for a given systolic volume. These two physical phenomena proper of the cardiovascular system are important factors in regulating the blood pressure and cardiac debt.

From this concept, it was possible to develop several possible applications of the passive chamber acting as a blood pumping device, aortic counterpulsation, dampening the systolic pressure and assistance of diastolic pressure.

Further, arterial hypertension is a polygenic syndrome and it comprises genetic, environmental, vascular, hormonal, renal and neural aspects. The essential or primary arterial hypertension (HA) is one of the most common causes for cardiovascular diseases, affecting nearly 20% of the adult population in industrialized societies. The disease is a risk factor for coronary disease development, it accelerates atherosclerosis process and could be a determining factor for the early appearance of cardiovascular morbidity and mortality associated to the coronary disease, congestive heart failure, cerebrovascular accident and end-stage renal failure. The therapy for arterial hypertension is the reduction of cardiovascular morbidity and mortality, generally, the arterial pressure values to be reached with the treatment are: AP<140/90 mmHg in general population and AP<130/80 mmHg for diabetic hypertensive patients or patients suffering from nephropathy. In order to achieve this goal in terms of arterial pressure level, non-pharmacological and pharmacological measures are applied. However, when the goal is not reached even with the simultaneous use of at least three antihypertensive drugs from different classes, hypertension is classified as resistant. In this scenario, the percutaneous approach for the bilateral renal sympathetic denervation (RSD) using ablation procedure for radiofrequency has been used as an available therapeutic strategy and it is based on the knowledge that, among the various pathophysiological mechanisms involved in the resistance to the control of HA, it outstand the excessive stimulation of the renal sympathetic nervous system. Currently, the percutaneous interventionist technique named renal sympathetic denervation (RSD) using a catheter coupled to a radiofrequency device is used. This type of device produces radiofrequency shots that are applied in the renal artery wall by a catheter. Several models of these devices have been developed to perform the RSD, but the lack of broader studies about the cost effectiveness of the procedure, its application in large scale should not be recommended and shall be indicated only for true resistant hypertensive patients, group of a very high cardiovascular risk.

Considering these treatment options for arterial hypertension, we sought to develop an application form for the artificial circulatory assistance object of the present invention that could benefit the patients suffering from arterial hypertension resistant to the treatments currently available. In view of this objective, it was conceived a structure containing an inlet and an outlet in such way that occurs a longitudinal flow, in physiological anatomic model for blood pumping. The longitudinal form allows the blood circulation without causing a stagnation point of blood circulation, which solves a coagulation problem.

Thus, the setting of the chamber for artificial circulatory assistance object of the present invention, as illustrated in FIG. 7, comprises a rigid capsule (10), preferably made in transparent polycarbonate with a base (11) and a dome (12), preferably with external concave walls, said dome (12) provided with blood inlet connectors (13) and blood outlet connectors (14) and said inlet (13) and outlet (14) connectors positioned in series. Internally, the chamber for artificial circulatory assistance comprises an impermeable membrane (20) that divides in two compartments the rigid capsule interior (10), being one blood compartment (17), internal space wherein the blood flows, and the other, an external compartment (18) that is filled with gaseous volume.

In this setting, the blood flow runs through the blood compartment (17) of the membrane (20) and transmits pressure and volume to the external compartment (18) that is in the periphery, reproducing, this way, two attributes of the vascular system, the extensibility and the aortic capacitance.

The chamber for artificial circulatory assistance object of the present invention is implantable and can be removed, differently from the treatment with RSD that promotes permanent injury in the renal artery innervation, as well as sympathectomy. Furthermore, the chamber for artificial circulatory assistance object of the present invention promotes the following effects and advantages: (i) optimizes the vascular extensibility and aortic capacitance when damping systolic pressure peak and absorbing blood volume, (ii) increases diastolic pressure—in diastole the chamber releases the volume and pressure absorbed during systole for circulation, (iii) minimizes the peripheral vascular resistance, (iv) minimizes the arterial pressure, (v) minimizes the heart post charge work, (vi) increases the cardiac debt.

In general, the chamber for artificial circulatory assistance object of the present invention, when providing the effects above mentioned, reduces the risk of occurring complications inherent to the disease, such as cerebrovascular accident (CVA), acute myocardial infarction (AMI) and other morbidity states, still reducing the mortality rate associated to arterial hypertension.

First Variant Form

Figure 8:
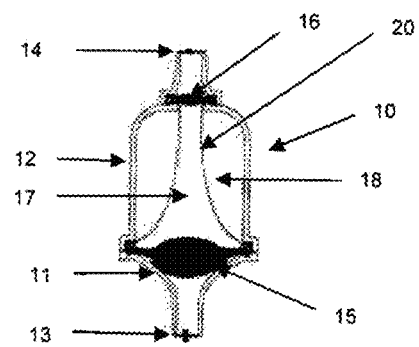
FIG. 8 illustrates a schematic sectional view from a first variant form of the chamber for circulatory assistance according to the present invention.

The chamber for artificial circulatory assistance object of the present invention, as illustrated in FIG. 8, reproduces the reciprocating pumping such as the heart, and the inlet (15) and outlet (16) unidirectional valves work to assure the pulsatile flow with systolic and diastolic phases. For doing so, the chamber for artificial circulatory assistance comprises a rigid capsule (31), preferably made in transparent polycarbonate and cylindrical body, base (11) and dome (12), preferably with external concave walls, provided with blood inlet connectors (13) and blood outlet connectors (14) positioned in series, and further the said chamber provided with respective one-way valves (15, 16). Internally, the chamber for artificial circulation assistance also comprises an impermeable membrane (20) that divides in two compartments the internal rigid capsule (10), one blood compartment (17), inner space wherein the blood flows, and the other, an external compartment (18) that is filled with compressible gaseous volume, which varies in two defined volumes and alternating occurrence, said objective is to provide, in each cycle, the filling and the emptying of the said rigid capsule (10).

The interaction between the pressure variation of the two sides of the impermeable membrane and the inlet and outlet one-way valves (15, 16) assembled in series produces a kinetic movement similar to the physiological cardiac blood flow, according illustration in FIG. 5.

The chamber for artificial circulatory assistance thus introduces into the extracorporeal circulation, several advantages still not reached by those from the prior art, which are (i) it is a device that simulates the circulatory physiology, applying the concept of active pulsatile flow associated to the counterpulsation concept, (ii) its application decreases the extracorporeal circuit tubes length, contributing for reducing blood hemodilution, (iii) produces less hemolysis, (iv) eliminates the effects produced by the use of linear flow.

The person skilled in the art will appreciate various other advantages provided by the chamber for artificial circulatory assistance object of the present invention when applied in extracorporeal circulatory systems (ECC).

For example, the chamber for artificial circulatory assistance object of the present invention can be applied as a special blood pumping device wherein it makes use of part of the energy from the arterial pulsation wave for generating optimized diastolic arterial flow in opposite direction to the systolic arterial flow. The compressible gas that fills the external compartment (18) is compressed by the interaction between the pressure variance from the two sides of the membrane (20) and the work of the one-way valves (15, 16) assembled in series produces kinetic movement of the blood. Thus, it is possible to produce diastolic counterflow, i.e., blood volume accumulated in the systolic phase in the compressible compartment is restored by the same access during the circulation diastolic phase. The pumping flow takes place intermittently and in opposite direction to the arterial flow, occurring directly in the diastolic period using volume and pressure accumulated by the chamber in the systolic period. The "counterflow" has enough intensity to offer circulatory assistance required for dialysis treatment, ultrafiltration and ventilatory assistance. For doing so, it has to be installed in arterial access, preferably femoral arterial, considering the amplitude of the pulsation wave from this artery.

It will be apparent for the skilled person in this field that the chamber for artificial circulatory assistance object of the present invention will produce the following advantageous effects:

single arterial access, thus being possible to reduce the patient exposure to a new puncture, reducing the risks and complications inherent to this procedure;

counterpulsation, being possible alleviating systolic pressure peaks with the performance from the compressible compartment allowing the accumulation and volume in its interior in the systolic phase working as an aortic compliance coadjutant and, hence, in the diastolic phase, returns circulation the partitioned volume in the systolic phase, thus producing an important increase in the flow and diastolic pressure capable of producing counterflow in the arterial access line;

eliminates the arteriovenous shunt produced by this type of access, the shunt deviates part of the arterial flow, and this deviation decreases the blood flow from the arterial bed accessed, which leads to risks of ischemia and, in more severe cases, could lead to limb amputation;

produces an increase in blood flow on the accessed vessel;

uses the circulation energy from the patient himself for its functioning without requiring an electromechanical system.

Second Variant Form

Figure 9:
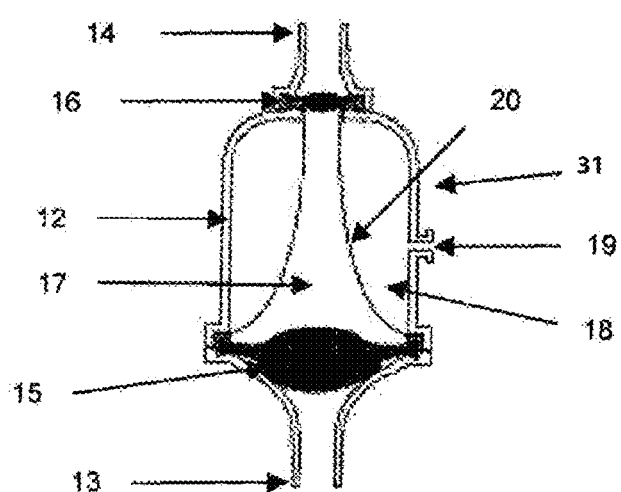
FIG. 9 illustrates a schematic sectional view from a second variant form of the chamber for circulatory assistance according to the present invention.

The chamber for artificial circulatory assistance object of the present invention could also assume a second structural setting, such as the setting illustrated in FIG. 9, when applied as a ventricular assistance device, by partial or total replacement of the blood pumping function in patients with poor heart function and that are indicated for mechanical circulatory assistance treatment.

In this configuration, the chamber for artificial circulatory assistance object of the present invention comprises a rigid capsule (31) preferably made of transparent polycarbonate and cylindrical body, base (11) and dome (12) with external concave walls, provided with blood inlet connectors (13) and blood outlet connectors (14), besides the respective one-way valves (15, 16), said inlet (13) and outlet (14) connectors being positioned in series. Internally, said chamber comprises an impermeable membrane (20) that divides in two compartments the rigid capsule (31) interior, being one blood compartment (17), an internal space wherein the blood flows, and the other an external compartment (18) that is filled with gaseous volume or injectable/exhaustible fluid. The gas or fluid is compressed by an external device connected to an inlet (19) by a proper connector. The interaction between pressure variation from the two sides of the membrane, i.e., the blood compartment (17) and external compressible compartment (18) together with the one-way valves (15, 16) functioning assembled in series produces the kinetic movement similar to the physiological cardiac blood flow.

In active state, in this variant configuration, blood comes to the chamber for artificial circulatory assistance by the base (11) as to the function of negative pressure generated by the fast removal of gas/fluid from the external compressible compartment (18). The chamber fills, the pressure equals and the one-way valve (15) of the base (11) closes. The external device delivers a determined volume of gas/fluid within the external compressible compartment (18), the gas is compressed and it transfers pressure to the blood. The one-way outlet valve (16) in the dome (12) opens allowing blood output. When the internal and the external pressure to the chamber are equal, the one-way outlet valve (16) closes restarting the cycle.

As it is known, during the application of the mechanical circulatory assistance devices from the prior art, generally it occurs some complications. Risks of bleeding, infectious conditions, microembolism, and blood clots formation due to the complexity of the procedure or related to the device technical limitation, are some examples of complication. It is added to such complications the contraindications, particular conditions wherein there is no therapeutic advantage and vascular access restriction.

The chamber for artificial circulatory assistance object of the present invention, structured as illustrated in FIG. 9, simulates the circulatory physiology, applying an active pulsatile flow concept associated to the counterpulsation concept. Thereby, heart muscle contraction work is well reduced (post charge) with the action of the passive chamber when maximizing the aortic compliance and "assisting" the cardiac systole. The term assistance is very pertinent, because in the ventricular ejection moment that corresponds to the point of myocardial greater effort, the myocardial has to produce required strength for ejecting a given blood volume against a highly resistant compartment. In this moment, the chamber for artificial circulatory assistance object of the present invention acts reducing the peripheral vascular resistance by emptying its air part and, at the same time, facilitates the ventricular ejection. Thus, it is set forth that the heart is kept in a relative resting state with low energetic spent and low oxygen consumption. Furthermore, the chamber for artificial circulatory assistance object of the present invention, right after the cardiac cycle, produces an increase in diastolic pressure by filling its air compartment. This effect produces greater cardiac debt and, thus, greater tissue perfusion.

Furthermore, the chamber for artificial circulatory assistance object of the present invention is compact, with little volume, it can be implemented in paracorporeal or intracavity mode, it is connected to an external drive by means of a compressed air line with variable extension. It is equipped with one-way valves, preferably of cartwheel type, that is characterized by a flow passage between its radiuses. This feature allows blood flow without circulation stagnation points, phenomenon faced by other devices equipped with semilunar valves and it has as a consequence formation and releasing of blood clots in the circulation.

Additionally, the chamber for artificial circulatory assistance object of the present invention produces less blood trauma, because it does not subject the blood flow to high rotations and does not require presential assistance of a clinical perfusionist at the bedside.

Third Variant Form

Figure 10:
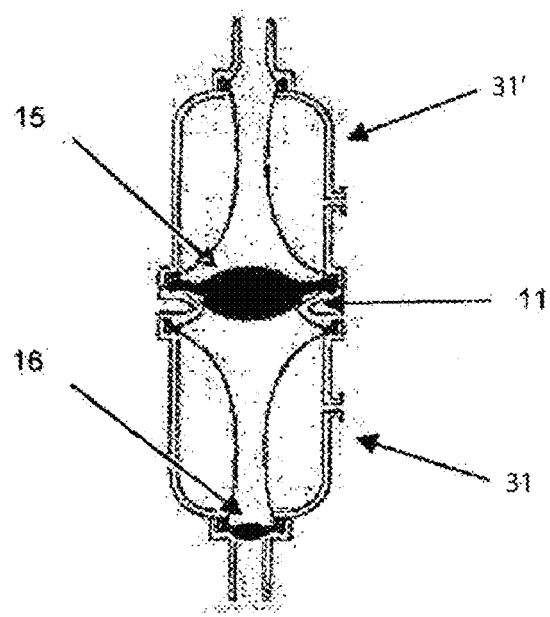
FIG. 10 illustrates a schematic sectional view from a third variant form of the chamber for circulatory assistance according to the present invention.

The chamber for artificial circulatory assistance object of the present invention could also assume a third structural setting, such as the setting illustrated in FIG. 10, when applied as ventricular assistance device, by partial or total replacement of the blood pumping function in patients with poor heart function and that are indicated for mechanical circulatory assistance treatment. In such configuration, the chamber for artificial assistance object of the present invention comprises two rigid capsules (31, 31'), interconnected in series through their bases, being one inverted in relation to the other and having one one-way valve (16) positioned at the inlet connector of the first chamber (31) for artificial circulatory assistance and other one-way valve (15) positioned between the first chamber (31) and the second chamber (31') for artificial circulatory assistance.

Membrane

Figure 11:
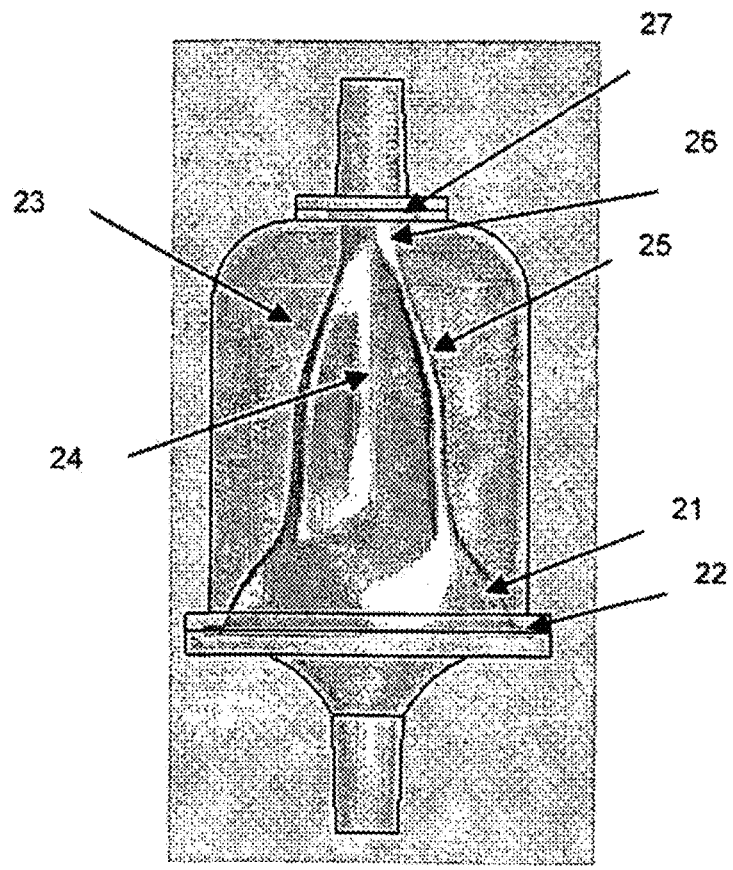
FIGS. 11, 12 and 13 illustrate, respectively, in frontal, perspective and superior view, a membrane according to the present invention.
Figure 12:
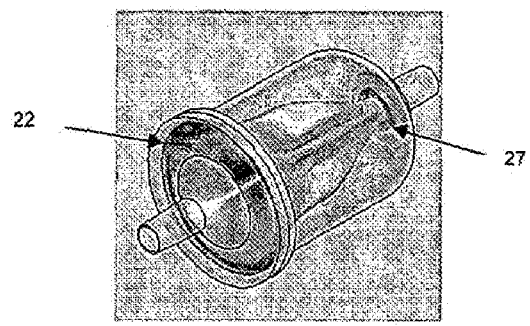
Figure 13:
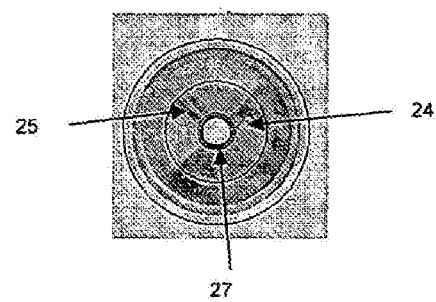

The present invention also refers to a thin walled membrane as illustrated in FIGS. 11 to 13. It is observed in these figures that the membrane (20) comprises a circular base (21) with a bigger diameter opening having a flap (22) for adapting in the capsule (10), a superior end (26) with a circular shape with a smaller diameter opening, wherein it has a flap (27) for adapting in the opposite end of said capsule (10), and a body (23) having a shape that projects upwards from the circular base (21) opening and narrows forming a plurality of vertical folds (24) and a plurality of vertical indentations (25) arranged alternatively up to its superior end opening (26), and changes progressively its shape from the circular shape of the base with a big diameter opening to a circular shape with a smaller diameter opening at its superior end (26). As the circular base (21) and the circular superior end (26) of the membrane are open and positioned in series, the shape of said membrane forms an internal fluid compartment wherein fluid flows longitudinally through this internal compartment, from one end to the other end of said membrane.

The membrane (20) must perfectly engage in the capsule (10) interior in a fixed and hermetic manner, being made of completely impermeable material.

Said membrane could be, obviously, used in other types of different cocoon of the capsule (10), depending only on aspects related to specific projects and uses, because of that it could assume various shapes, since its specific intrinsic characteristics are preserved, such as the ones herein described.

Figure 14:
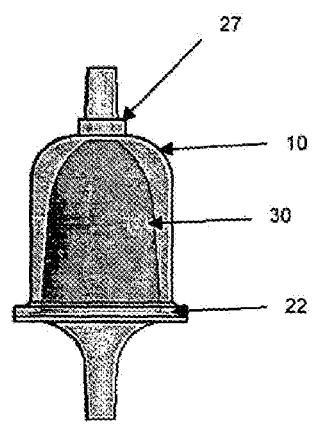
FIG. 14 illustrates a frontal view from a variant form of a membrane according to the present invention.
Figure 15:
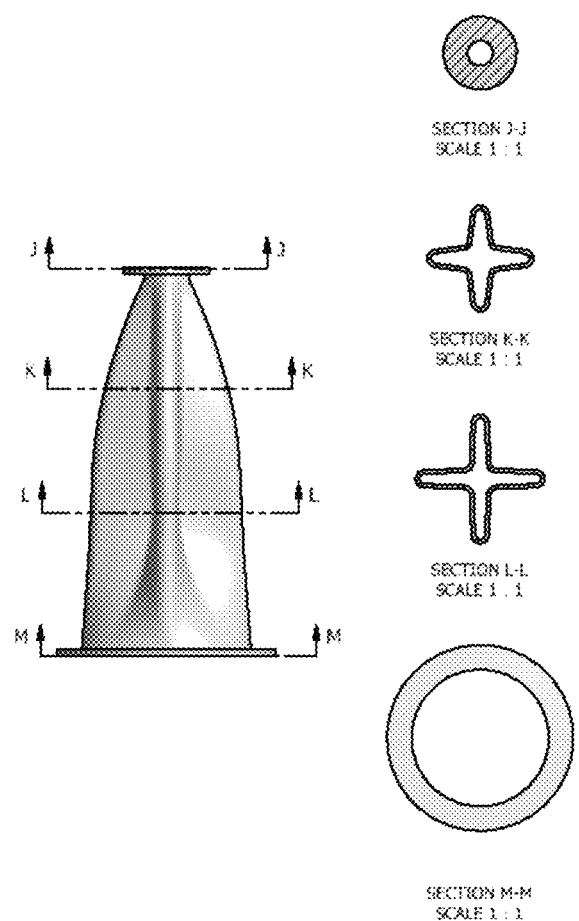
FIG. 15 illustrates the cross section views of the membrane of an embodiment of the present application.

An example of a variant form is the one illustrated in FIG. 14, developed to be applied in a chamber acting under negative pressure, which is especially adequate to be applied in the pump inlet line in order to reduce pressure oscillations. In this configuration, said membrane also has a circular base opening with a flap (22) and a superior end opening having the flap (27) in such a way that can be perfectly engaged into the chamber interior shaped as a capsule (10), in a fixed and hermetic manner. However, said membrane has a body that extends upwards from the circular base opening progressively and smoothly changing its diameter from the circular base opening with bigger diameter to the opposite end opening with smaller diameter.

The invention claimed is:

1. A membrane made of impermeable material for a fluid circulation chamber, said fluid circulation chamber comprising a capsule, an inlet connector, and an outlet connector to provide fluid circulation, wherein the membrane comprises:
   a circular base with a first opening having a first flap for adapting in the capsule, in a fixed and hermetic manner;
   a superior end with a circular shape with a second opening, wherein it has a second flap for adapting in an opposite end of said capsule, in a fixed and hermetic manner;
   a body having a shape that projects upwards from the first opening of the circular base and narrows forming a plurality of vertical folds and a plurality of vertical indentations arranged alternatively up to the second opening of the superior end, wherein a diameter of the first opening is bigger than a diameter of the second opening.

2. A fluid circulation chamber for artificial circulatory assistance to be used as an arterial pulse wave damping device, comprising:
   a capsule having a base and a dome, provided with an inlet connector and an outlet connector positioned in series,
   wherein the fluid circulation chamber internally comprises the membrane according to claim 1, wherein the capsule is a rigid capsule, the membrane divides an interior of the capsule into two compartments, comprising:
   an internal fluid compartment, defined by an internal wall of the membrane, where a fluid flows through from the inlet connector to the outlet connector, and
   an external compressible compartment, defined between an external wall of the membrane and an internal wall of the capsule, wherein the external compressible compartment is filled with gaseous volume,
   wherein a volume of the internal fluid compartment varies due to flow and pressure variations inside it, causing compression and decompression of the gaseous volume of the external compressible compartment, causing a pressure variation in the external compressible compartment in response to the flow and pressure variations,
   the volume of the internal fluid compartment can vary between maximum and minimum volumes, providing fulfillment and emptying of the internal fluid compartment in each cycle and reducing an amplitude of the pressure and flow variations.

3. The fluid circulation chamber for artificial circulatory assistance of claim 2, further comprising a one-way valve at the inlet connector and a one-way valve at the outlet connector, wherein an interaction between the pressure variations on both sides of the membrane, and the one-way valves assembled in series at the inlet connector and the outlet connector are configured to produce kinetic movement similar to physiological cardiac blood flow.

4. The fluid circulation chamber for artificial circulatory assistance of claim 3, wherein the fluid is blood when the fluid circulation chamber is applied in a provisional or definitive implantable medical device for acting as a cardiovascular orthosis or prosthesis for extracorporeal circulation.

5. The fluid circulation chamber for artificial circulatory assistance of claim 4, wherein the capsule is made of transparent polycarbonate.

6. The fluid circulation chamber for artificial circulatory assistance of claim 4, wherein the one-way valves are of a Cartwheel type.

7. The fluid circulation chamber for artificial circulatory assistance of claim 3, wherein fluid flows through from the inlet connector to the outlet connector, and
   the external compressible compartment is filled with gaseous volume or injectable/exhaustible fluid by an external device connected to an inlet through an adequate connector located at an external wall of the rigid capsule when the fluid circulation chamber is used as a ventricular assistance device.

8. The fluid circulation chamber for artificial circulatory assistance of claim 7, wherein the capsule is made of transparent polycarbonate.

9. The fluid circulation chamber for artificial circulatory assistance of claim 7, wherein the one-way valves are of a Cartwheel type.

10. The fluid circulation chamber for artificial circulatory assistance of claim 3, wherein the capsule is made of transparent polycarbonate.

11. The fluid circulation chamber for artificial circulatory assistance of claim 3, wherein the one-way valves are of a Cartwheel type.

12. An assembly of the fluid circulation chambers of claim 2 for artificial circulatory assistance, comprising:
   a first fluid circulation chamber and a second fluid circulation chamber, wherein the first fluid circulation chamber and the second fluid circulation chamber are interconnected in series through their bases;
   a one-way valve positioned at the inlet connector of the first fluid circulation chamber; and
   an other one-way valve positioned between the first fluid circulation chamber and the second fluid circulation chamber,
   wherein an external device connected to an inlet through an adequate connector located at an external wall of the rigid capsule of the first fluid circulation chamber.

13. The fluid circulation chamber for artificial circulatory assistance of claim 12, wherein the capsule is made of transparent polycarbonate.

14. The fluid circulation chamber for artificial circulatory assistance of claim 12, wherein the one-way valves are of a Cartwheel type.

15. The fluid circulation chamber for artificial circulatory assistance of claim 2, wherein the capsule is made of transparent polycarbonate.

16. A membrane made of impermeable material for a fluid circulation chamber acting under negative pressure for applying in a pump inlet line, the fluid circulation chamber comprising a capsule, an inlet connector, and an outlet connector to provide fluid circulation, wherein the membrane comprises:
- a circular base with a first opening having a first flap for adapting in the capsule;
- a superior end with a second opening having a second flap for adapting in an opposite end of the capsule, wherein a diameter of the first opening is bigger than a diameter of the second opening;
- a body that extends upwards from the circular base and changes its diameter progressively and smoothly from the first opening of the circular base with bigger diameter to the second opening at the superior end with smaller diameter.

17. A fluid circulation chamber for artificial circulatory assistance to be used as a negative pulse wave damping device, comprising:
- a capsule being rigid and having a base, provided with an inlet connector and an outlet connector positioned in series;
- the membrane according to claim 16, which divides the capsule interior in two compartments, comprising:
- an internal fluid compartment, defined by an internal wall of the membrane, where a fluid flows through from the inlet connector to the outlet connector, and
- an external compressible compartment, defined between an external wall of the membrane and an internal wall of the capsule, wherein the external compressible compartment is filled with gaseous volume,
- wherein a volume of the internal fluid compartment varies due to flow and pressure variations inside the internal fluid compartment, causing compression and decompression of a gaseous volume in the external compressible compartment in response to the flow and pressure variations,
- the volume of the internal fluid compartment can vary between a maximum volume and a minimum volume, providing fulfillment and emptying of the internal fluid compartment in each cycle and reducing an amplitude of the pressure and flow variations.

18. The fluid circulation chamber for artificial circulatory assistance of claim 17, wherein the capsule is made of transparent polycarbonate.

* * * * *